United States Patent [19]
Upton

[11] Patent Number: 5,968,507
[45] Date of Patent: *Oct. 19, 1999

[54] METHOD FOR REMOVING NITS FROM HAIR

[75] Inventor: Harry F. Upton, Darien, Conn.

[73] Assignee: Care Technologies, Inc., Darien, Conn.

[*] Notice: This patent is subject to a terminal disclaimer.

[21] Appl. No.: 08/688,303

[22] Filed: Jul. 30, 1996

Related U.S. Application Data

[63] Continuation of application No. 08/296,277, Aug. 25, 1994, Pat. No. 5,547,665, which is a continuation of application No. 08/046,565, Apr. 13, 1993, abandoned.

[51] Int. Cl.⁶ ........................................................ A61K 7/48
[52] U.S. Cl. .......................................... 424/94.61; 424/70.1
[58] Field of Search ................................ 424/94.61, 70.1; 514/747, 880

[56] References Cited

U.S. PATENT DOCUMENTS 4,863,725  9/1989  Deckner et al. .......................... 424/81

*Primary Examiner*—Jyothsna Venkat
*Attorney, Agent, or Firm*—Ohlandt, Greeley, Ruggiero & Perle

[57] ABSTRACT

A method for removing nits (e.g., lice eggs) from hair which comprises the application of a water-based enzyme composition to the hair, whereby the water-based enzyme composition is capable of causing swelling and/or biodegrading of the complex organic structure that cements nits to the hair to facilitate the subsequent physical removal of the nits from the hair.

28 Claims, No Drawings

METHOD FOR REMOVING NITS FROM HAIR

This is a continuation of application Ser. No. 08/296,277 filed on Aug. 25, 1994, now U.S. Pat. No. 5,547,665, which in turn is a continuation of application Ser. No. 08/046,565, filed on Apr. 13, 1993, now abandoned.

The present invention generally relates to the application of a pre- or post-pediculicide water-based enzyme composition in conjunction with a lice-killing pediculicide for the removal of nits (i.e., lice eggs) from a patient's hair. This pre- or post-pediculicide product is capable of causing swelling and/or biodegrading of the complex organic structure that cements nits to the hair to facilitate the subsequent physical removal of the nits from the hair.

BACKGROUND OF THE INVENTION

The head louse (pediculus humanus capitit) infests roughly 2–3% of grade school children in the United States and England. The females, about ⅛ inch long, deposit approximately 270–300 eggs, most commonly on the hair above the ears and the back of the head near the base of the hair shaft. The eggs are cemented to the hair with a tenacious protein-like substance.

Head lice are capable of spreading disease. Specifically, head lice are vectors for staphylococcal skin infections, e.g., impetigo, furunculosis, and are also the principle method of transmission for typhus, trench fever, and relapsing fever.

Effective control of head lice can be obtained with a number of insecticides (termed pediculicides for this application), such as malathion, carbaryl, lindane, pyrethrins and piperonyl butoxide, and the synthetic pyrethrin analog permethrin. The most acceptable treatments involve shampoos which contain the pediculicide, some of which are prescription products (e.g., lindane). Some eggs, however, often survive the treatment.

Physical removal of the lice can be accomplished to a significant degree with hair washing followed by thorough brushing. Fine toothed nit combs, which are designed for removal of the nits anchored to the hair shaft, are not particularly effective in removing the eggs. If still alive, the eggs can lead to a full reinfestation of the hair. If dead, following pediculicide treatment, they can still represent a social embarrassment for both child and parent, with no absolute certainty that the nits are all dead and therefore potentially reinfesting.

Furthermore, children must be nit free to return to school even if a lice treatment is resident on the head. Therefore, efforts have recently been directed to develop products which are effective in unlocking the bond between the lice egg and the hair. One such product is marketed under the trademark STEP 2® by GenDerm as a lice egg removal kit. STEP 2® is a liquid treatment that attempts to loosen the bond between lice eggs and hair to facilitate nit removal via a fine tooth comb. STEP 2® has a formic acid base which is a harsh chemical and produces an unpleasant odor. It also contains polyquaternium, benzyl alcohol and cetyl alcohol as preservatives. However, contrary to the claims made by the manufacturer of STEP 2®, it has been determined by the present inventor that STEP 2® does not provide any practical ability to loosen nits to facilitate removal by combing. Finally, STEP 2® does not break down pesticidal shampoo toxins.

The present invention, however, does satisfactorily remove lice eggs from hair stands. When used as a post-pediculicide treatment it is capable of removing pediculicide product residue and the odor associated therewith to leave treated hair clean and fresh smelling. It uses a water-based enzyme composition that attacks the cement-like complex organic structure that bonds the nit to the hair causing swelling and/or biodegrading of the complex organic structure to facilitate the subsequent physical removal of the lice nits from the hair. When it acts as a biodegrader it converts the complex organic structure to another non-bonding composition, e.g., a sugar. As such, it is a natural, vegetable derived enzyme, chemical-free and non-toxic composition which attacks and rapidly swells and/or biodegrades the complex organic structure that comprises the louse glue. Moreover, the water-based enzyme composition of the present invention is effective in breaking chemical bonds, resulting in the biodegrading of pediculicide residues on the hair and scalp of the patient. Furthermore, the water-based enzyme composition does not react to the protein structure of the hair and it is non-irritating to the skin and mucous membranes. It also leaves the treated hair soft, silky and fresh smelling.

The present invention also provides many additional advantages which shall become apparent as described below.

SUMMARY OF THE INVENTION

A method for removing nits from hair which comprises the application of a water-based enzyme composition to the hair. The water-based enzyme composition may include an enzyme, a stabilizer and/or a surfactant.

Preferably, the enzyme-based composition is applied to the hair either prior or subsequent to treatment with a pediculicide composition. Moreover, the method further comprises the step of removing the lice eggs or nits from the hair after they have been dislodged therefrom.

Furthermore, the present invention provides a method for removing nits from hair which comprises the following steps of applying a pediculicide to the hair of a host, removing the pediculicide from the hair after all or a substantial portion of the nits are killed, applying a water-based enzyme composition which is capable of causing the swelling and/or breaking down of the complex organic structure that bonds the nits to the hair, thereby facilitating the dislodging of the nits from the hair, and removing the dislodged nits from the host.

Additionally, the present invention provides a method for removing nits from hair which comprises the following steps of applying a water-based enzyme composition which is capable of causing the swelling and/or breaking down the complex organic structure that bonds the nits to the hair, thereby facilitating the dislodging of the nits from the hair, removing the water-based enzyme composition, applying a pediculicide to the hair of a host, removing the pediculicide from the hair after all or a substantial portion of the nits are killed, and removing the dislodged nits from the host.

Other and further objects, advantages and features of the present invention will be understood by reference to the following specification.

DESCRIPTION OF THE PREFERRED EMBODIMENTS

The nit removal product of the present invention is a water-based enzyme composition capable of causing the swelling and/or breaking down of complex organic structures, e.g., chitin, which are fundamentally carbohydrate-based. The water-based enzyme composition may be selected from three different classes standardized by activity. The three classes of enzymes are lyases, oxidoreductases, and hydrolases.

Enzymes are organic catalysts produced by living organisms. They are invariably proteins, which are generally water soluble or colloidal, and are characterized by their great activity, specificity, susceptibility to the influence of pH, temperature, trace elements and other environmental changes.

Hydrolases are enzymes that cleave specific bonds through the addition of the water molecule (H—OH) to the cleaved fractions. The hydrolases are further subdivided according to the nature of their substrates or reactants, where the suffix "ase" is attached to the name of the substrate. Thus the esterases hydrolyze esters, carboproteins, peptidases and amidases hydrolyze peptides (fractions of proteins) and amides, respectively, etc. Within each group, such as the carbohydrases, the individual enzyme is characterized by the specific substrate upon which it acts, such as B-D-galactosidase (lactase), which hydrolyzes the individual bonds of the polymer chain of N-acetyl-glucosamine (chitin). Another enzyme, termed an acetamidase, might exist to sever the acetamide side-chain from the chitin polymer, without disrupting the basic carbohydrate polymer.

Lyase-ligase systems are a special class of transferase enzymes, which catalyze either the formation of new carbon-carbon bonds (ligase), or the splitting of such bonds (lyase).

Oxidizing enzymes are a large group of enzymes which catalyze oxidation-reduction reactions. "Oxidoreductases" are further classified into oxygenases or hydroxylases and dehydrogenases. The latter are often further characterized on the basis of their co-enzymes.

Since chitin has been identified by one researcher as the binding substance between the nit and the hair shaft (and in fact is the basic component of the lice egg case), and since its primary chemical classification is that of a carbohydrate, the present invention is primarily directed to that class of enzymes which are particularly effective in breaking down D-glucose polymers, such as starch and cellulose, i.e., glucosidases, and more specifically the N-acetyl-D-glucosaminidases. It is believed that these enzymes containing acetamidase which are capable of splitting the side chain off of the chitin polymer, thereby rendering the remaining chain more susceptible to the absorption of water and subsequent swelling.

The enzymes used in the present invention are capable of breaking down, degrading many organic compounds, or interfering with the adhesion of the organic compounds to hair protein. This chain of reactions is the fundamental reason why the nit removal product of the present invention is able to facilitate the cleansing from hair of chemical pesticides and unwanted residues, as well as weakening the bond between the nits and the hair shaft.

The present invention provides a novel method for removing nits from hair which comprises the following steps: applying a pediculicide to the hair of a host; removing the pediculicide from the hair after a substantial portion of the nits are killed; applying a water-based enzyme composition which is capable of causing the swelling and/or breaking down of the complex organic structure that bonds the nits to the hair, thereby facilitating the dislodging of the nits from the hair; and removing the dislodged nits from the host. Alternatively, the water-based enzyme composition may be added prior to treatment with the pediculicide, if it is desired to retain a pesticide residue.

One preferred water-based enzyme composition is set forth in U.S. Pat. No. 5,108,746 (Rho et al.), which issued on Apr. 28, 1992, and which is incorporated herein by reference. Preferably, the water-based enzyme composition comprises at least one enzyme selected from the group consisting of lyase, oxidoreductase and hydrolase, which is stabilized against microbial growth by the addition of effective amounts of a water soluble salt of a carboxylic acid and a potentiating amount of an alkylolated urea possessing a heterocyclic ureido substituent, or the interaction product of the carboxylic acid and the alkylolated urea.

The Rho et al. patent does not describe or suggest the use of a water-based enzyme composition to remove nits from hair. The water-based enzyme composition of Rho et al. was specifically intended for use as shampoos, cleansing creams, cosmetics, eye preparations, body lotions, pharmaceuticals, physiological saline solutions, odor and stain eradicators, disinfectants, suppositories and the like.

The water soluble salt of a carboxylic acid is preferably a benzoate (e.g., sodium benzoate, potassium benzoate and alkyl para-amino benzoates) and the alkylolated urea compound selected from the group consisting of diazolidinyl urea and imidazolidinyl urea. The benzoate and the urea compound are preferably used in a weight ratio of from about 0.5:1 to about 1:0.05, more preferably from about 1:1.

The alkylolated urea compound possesses a heterocyclic ureido substituent of the formula:

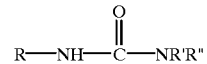

wherein each of R and R" may be one of hydrogen, alkyl (preferably lower alkyl, such as alkyl containing 1–4 carbon atoms), hydroxyalkyl (preferably) lower alkyl, such as alkyl containing 1–4 carbon atoms), and alkoxyalkyl (preferably lower alkyl in each case, such as alkyl containing 1–4 carbon atoms), or R', and R' may be a heterocyclic group of the formula:

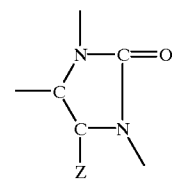

wherein one of the free valences thereof is bonded to the nitrogen of the urea, and the remaining free valences are bonded to one of the hydrogen, alkyl (preferably lower alkyl, such as alkyl containing 1–4 carbon atoms), hydroxyalkyl (preferably lower alkyl, such as alkyl containing 1–4 carbon atoms), and alkoxyalkyl (preferably lower alkyl in each case, such as alkyl containing 1–4 carbon atoms), Z satisfies the free valence of the carbon atom to which it is bonded and may be oxo, hydrogen, hydroxyalkyl, alkyl, monovalent heterocyclic radicals containing a ring bonded

where the free valences of the nitrogen are saturated, and the like moieties.

The term "interaction product," as used herein and in the claims, means the association of carboxylic acid and urea by molecular attraction ranging from strong to weak bonding relationships, including without limitation, covalent bonding, ionic bonding, Van der Waal forces, hydrogen bonding and/or associative bonding.

The water soluble salt of a carboxylic acid includes those carboxylic acids that posses inhibitive effects toward bacterial contamination. An attribute of the acid is that in the salt-free form, it is not normally soluble in water, or is essentially water insoluble. Desirable water insoluble acids are the aromatic carboxylic acids such as those set forth in U.S. Pat. No. 5,108,746, which are incorporated herein by reference. The salt forming component suitable in solubilizing the aforementioned acids include the alkali metal salts, the quaternary ammonium salts, and the like. Suitable salt forming cations are set forth in U.S. Pat. No. 5,108,746, which are incorporated herein by reference.

The most preferred compositions for use in nit removal comprise a water-based enzyme composition which is capable of causing swelling and/or breaking down of the complex organic structure that bonds the nits to the hair, thereby facilitating the dislodging of the nits from the hair. The enzyme composition comprising at least one enzyme selected from the group consisting of lyase, oxidoreductase and hydrolase. The water-based enzyme composition is stabilized against microbial growth by the addition of an alkali metal salt of benzoic acid, and diazolidinyl urea and/or an imidazolidinyl urea.

These compositions allow the production of water-based enzyme compositions that are stabilized against bacterial contamination and have a shelf life or stability of about two years or more. Moreover, such stabilized compositions are environmentally acceptable and safe to humans and animals who are exposed to or contact them.

The salt of carboxylic acid and the urea compound, such as, sodium benzoate and diazolidinyl urea or imidazolidinyl urea stabilizers, can be added individually to the water-based formulations in the appropriate amounts in order to obtain the desired stabilization. However, it is preferred that stabilizing compositions comprising mixtures of the two stabilizers be formed and that an appropriate effective stabilizing amount of a stabilizing composition be added to the water-based treatment system.

The amounts of the salt of the carboxylic acid and the urea compounds are not narrowly critical. Typically, they may be used in a weight ratio of from about 0.1 to 10 of either the salt or the urea compound to the other. For example, where the stabilizing compositions comprise sodium benzoate and an effective bacterial stabilizing amount of diazolidinyl urea or imidazolidinyl urea, such stabilizing compositions will generally comprise sodium benzoate and diazolidinyl urea or imidazolidinyl urea in a weight ratio of from about 0.5:1 to about 1:0.5, most preferably in a weight ratio of about 1:1. The optimum stabilizing composition comprises a 1:1 mixture of sodium benzoate and diazolidinyl urea or imidazolidinyl urea.

The amount of such stabilizing composition added to water-based enzyme compositions to stabilize them against bacterial contamination will be any bacterial effective stabilizing amount, generally from about 0.05 to about 2%, preferably from about 0.1 to about 1%, and most preferably from about 0.2 to about 0.5 wt. % of stabilizing composition based on the total weight of the water-based enzyme composition. It will be appreciated that the amount of stabilizing composition incorporated in the water-based enzyme compositions will vary with the type and components of the water-based enzyme compositions.

The amount of each stabilizing component employed in the water-based enzyme composition to stabilize the composition against bacterial contamination will generally be in an amount of from about 0.025% to about 1%, preferably from about 0.05% to about 0.5%, more preferably from about 0.1% to about 0.25%, and most preferably from about 0.1% by weight of each of the salt of the carboxylic acid, such as sodium benzoate, and the urea compounds, such as diazolidinyl urea or imidazolidinyl urea.

A preferred enzyme is the commercially available enzyme containing a water-based product, VETCAIR™, licensed to Nature Plus Inc. of New Canaan, Conn.

The preferred composition according to the present invention comprises an enzyme stabilized with 0.1% by weight sodium benzoate and 0.1% by weight imidazolidinyl urea. This composition exhibits effective bacterial contamination control by rapidly reducing and essentially eliminating the contaminating bacterial inoculums in the products. The combination of sodium benzoate and diazolidinyl urea not only synergistically protects water-based compositions against microbial contamination, but is considered environmentally acceptable and safe to humans and animals.

The water-based enzyme composition preferably includes at least one surfactant selected from the group consisting of: alkanolamides, alkylaryl sulfonates, and ethoxylated derivatives, amine oxides, betaine derivatives, ethoxylated alcohols, ethoxylated alkylphenols, ethoxylated amines, ethoxylated fatty acids and sulfonates, glycol esters, imidazolines and their derivatives, and quaternary compounds. The surfactants assist in wetting the chitin-hair interface and facilitates the swelling (hydration)/enzymatic action.

In order to exemplify the effectiveness of the water-based enzyme composition verses the conventional STEP 2® program, the following comparison tests were conducted.

EXAMPLE 1

A study was carried out using both the water-based enzyme composition of the present invention and the STEP 2® product in order to determine their respective efficiencies in removing lice eggs (i.e., nits) attached to human hair.

Each of the two products was applied, in two separate trials, to individual strands of nit-bearing hair which has first been pre-wet with warm water for five minutes. The strands were blotted dry and both products then applied full strength, either as a gel (i.e., STEP 2®) or spray.

For the STEP 2® treatment, the product was left on for 10 minutes, and then rinsed well with water and blotted dry. In both of the STEP 2® trials, thereafter, the individual strands were pulled twenty times through the teeth of a metal comb which was supplied with the STEP 2® package. This simulated combing of the hair. In neither trial was the nit removed after the twenty strokes.

For one trial of the water-based enzyme composition of the present invention, the spray was applied for one minute to a wet hair strand that had been blotted dry. Following the contact period, the product was rinsed off of the hair strand, which was then combed twenty times with a metal comb without removal of the nit. Thereafter an additional three minute spray application was made to the same moist hair strand. The spray was then rinsed away with water, the strand was blotted dry and again combed with a metal comb. During the fourth stroke the nit was removed.

For the second trial, a pre-moistened hair strand containing two head-louse eggs was treated with a spray application of the water-based enzyme composition of the present invention. After three minutes the product was rinsed away with water, the strand blotted dry, and then combed. After one stroke, one of the two eggs was removed. The second egg was removed during the fourth stroke.

The water-based enzyme composition was significantly more efficient that the commercial STEP 2® gel in removing hair lice eggs from hair strands. The gel showed no practical ability to loosen nits to facilitate removal by combing, while the composition of the present invention was most effective following a 3–4 minute exposure thereto.

EXAMPLE 2

The following example demonstrated that the treatment of hair with a water-based enzyme prior to pediculicide treatment also provided substantially reduced number of lice eggs attached to the hair strands after pediculicide treatment.

A water-based enzyme composition was liberally applied as a shampoo to the dry hair of an eight year old male. Hair length was approximately 3½" long. Prior to application, the head was observed for nits and lice. Approximately 30 nits were present and 5 live lice. The shampoo was worked until a slight foaming action was visible. The shampoo was left on for three minutes and then rinsed out with plain tap water.

Nix permethren pediculicide was then applied following the package instructions. The Nix application was left on the subject's head for ten minutes, then rinsed out thoroughly with water.

Proper combing technique was followed for removal of lice and nits. All visible nits and lice were readily combed out of the subject's hair.

While I have shown and described several embodiments in accordance with my invention, it is to be clearly understood that the same are susceptible to numerous changes apparent to one skilled in the art. Therefore, I do not wish to be limited to the details shown and described but intend to show all changes and modifications which come within the scope of the appended claims.

What is claimed is:

1. A method for removing nits from hair which comprises the application of a water-based enzyme composition to said hair, whereby said water-based enzyme composition is capable of causing swelling and/or biodegrading of the complex organic structure that cements said nits to said hair to facilitate the subsequent physical removal of said nits from said hair, and wherein said water-based enzyme composition comprises at least one enzyme selected from the group consisting of lyase, oxidoreductase and hydrolase.

2. The method according to claim 1 wherein said water-based enzyme composition further comprises a stabilizer.

3. The method according to claim 2 wherein said stabilizer comprises a water soluble salt of a carboxylic acid and an alkylolated urea compound.

4. The method according to claim 1 wherein said water-based enzyme composition further comprises a surfactant.

5. The method according to claim 4 wherein said surfactant is at least one compound selected from the group consisting of: alkanolamides, alkylaryl sulfonates, and ethoxylated derivatives, amine oxides, betaine derivatives, ethoxylated alcohols, ethoxylated alkylphenols, ethoxylated amines, ethoxylated fatty acids and sulfonates, glycol esters, imidazolines and their derivatives, and quaternary compounds.

6. The method according to claim 1 wherein said enzyme-based composition is applied to said hair prior to treatment with a pediculicide composition.

7. The method according to claim 1 wherein said enzyme-based composition is applied to said hair subsequent to treatment with a pediculicide composition.

8. The method according to claim 1 further comprising the step of removing said lice eggs from said hair after they have been dislodge from said hair.

9. A nit removing agent which comprises:
   a surfactant; and
   an enzyme capable of causing swelling and/or biodegrading of a complex organic structure that cements lice eggs to the hair, said enzyme being present in the agent in an amount sufficient to cause swelling and/or biodegrading of the organic structure when the agent is applied to the hair to facilitate the subsequent physical removal of the lice eggs from the hair, and wherein said enzyme is selected from the group consisting of lyase, oxidoreductase and hydrolase.

10. The nit removing agent according to claim 9 further comprising a stabilizer.

11. The nit removing agent according to claim 10 wherein said stabilizer comprises a water soluble salt of a carboxylic acid and an alkylolated urea compound.

12. A method for removing nits from hair which comprises the steps of:
   applying a pediculicide to the hair;
   removing the pediculicide from the hair after a substantial portion of the nits are killed;
   applying a water-based enzyme composition to the hair, wherein said water-based enzyme composition is capable of swelling and/or breaking down the complex organic structure that bonds the nits to the hair, and wherein said water-based enzyme composition comprises at least one enzyme selected from the group consisting of lyase, oxidoreductase and hydrolase thereby facilitating the dislodging of the nits from the hair;
   removing the dislodged nits; and removing the water-based enzyme composition from said hair.

13. The method according to claim 12 wherein said water-based enzyme composition further comprises a stabilizer.

14. The method according to claim 13 wherein said stabilizer comprises a water soluble salt of a carboxylic acid and an alkylolated urea compound.

15. The method according to claim 12 wherein said water-based enzyme composition further comprises a surfactant.

16. A method for removing nits from hair which comprises the steps of:
   applying a water-based enzyme composition to the hair of a host, wherein said water-based enzyme composition is capable of swelling and/or breaking down the complex organic structure that bonds the nits to the hair thereby facilitating the dislodging the nits from the hair; and wherein said water-based enzyme composition comprises at least one enzyme selected from the group consisting of lyase, oxidoreductase and hydrolase;
   removing the water-based enzyme composition from said hair;
   applying a pediculicide to the hair of said host;
   removing the pediculicide from the hair after a substantial portion of the nits are killed; and
   removing the dislodged nits from the host.

17. A method for removing nits from hair, said method comprising the application to the hair of a water-based enzyme composition, said water-based enzyme composition being one capable of swelling and/or biodegrading a complex organic structure that cements the nits to the hair to facilitate the subsequent physical removal of the nits from the hair, said water-based enzyme composition including at least one enzyme capable of breaking down D-glucose polymers.

18. The method of claim 17, wherein said at least one enzyme is a hydrolase.

19. The method of claim 18, wherein said water-based enzyme composition further comprises at least one additional enzyme selected from the group consisting of lyase and oxidoreductase.

20. A nit removing agent comprising:
   a water-based enzyme composition capable of swelling and/or biodegrading a complex organic structure that cements nits to hair to facilitate the subsequent physical removal of the nits from the hair, said water-based enzyme composition including at least one enzyme capable of breaking down D-glucose polymers.

21. The nit removing agent of claim 20, wherein said at least one enzyme is a hydrolase.

22. The nit removing agent of claim 21, wherein said water-based enzyme composition further comprises at least one additional enzyme selected from the group consisting of lyase and oxidoreductase.

23. A method for removing nits from hair, said method comprising:
   applying a pediculicide to the hair of a host;
   removing the pediculicide from the hair after a substantial portion of the nits are killed;
   applying a water-based enzyme composition to the hair of the host, said water-based enzyme composition being capable of swelling and/or biodegrading a complex organic structure that cements the nits to the hair, thereby dislodging the nits from the hair, said water-based enzyme composition including at least one enzyme capable of breaking down D-glucose polymers;
   combing the hair to remove the dislodged nits from the host; and
   removing the water-based enzyme composition from the hair.

24. The method of claim 23, wherein said at least one enzyme is a hydrolase.

25. The method of claim 24, wherein said water-based enzyme composition further comprises at least one additional enzyme selected from the group consisting of lyase and oxidoreductase.

26. A method for removing nits from hair, said method comprising:
   applying a water-based enzyme composition to the hair of a host, said water-based enzyme composition being capable of swelling and/or biodegrading a complex organic structure that cements the nits to the hair, thereby dislodging the nits from the hair, said water-based enzyme composition including at least one enzyme capable of breaking down D-glucose polymers;
   removing the water-based enzyme composition from the hair
   applying a pediculicide to the hair of the host;
   removing the pediculicide from the hair after a substantial portion of the nits are killed; and
   combing the hair to remove dislodged nits from the host.

27. The method of claim 26, wherein said at least one enzyme is a hydrolase.

28. The method of claim 27, wherein said water-based enzyme composition further comprises at least one additional enzyme selected from the group consisting of lyase and oxidoreductase.

* * * * *